United States Patent
Wada et al.

[11] Patent Number: 5,746,729
[45] Date of Patent: May 5, 1998

[54] SANITARY NAPKIN

[75] Inventors: Ichiro Wada; Hideki Kondo, both of Ehime-ken; Masataka Kinoshita, Kagawa-ken, all of Japan

[73] Assignee: Uni-Charm Corporation, Ehime-Ken, Japan

[21] Appl. No.: 777,860

[22] Filed: Dec. 31, 1996

Related U.S. Application Data

[63] Continuation of Ser. No. 546,256, Oct. 20, 1995, abandoned.

[30] Foreign Application Priority Data

Oct. 27, 1994 [JP] Japan ................................. 6-263963

[51] Int. Cl.$^6$ ........................ A61F 13/15; A61F 13/20
[52] U.S. Cl. ...................... 604/378; 604/380; 604/382
[58] Field of Search ................................ 604/366, 365, 604/370, 378–385.1

[56] References Cited

U.S. PATENT DOCUMENTS 4,839,216 6/1989 Curro et al. .......................... 604/358

Primary Examiner—John G. Weiss
Assistant Examiner—Ki Yong O
Attorney, Agent, or Firm—Lowe Hauptman Gopstein & Berner

[57] ABSTRACT

A sanitary napkin includes a top layer having an upper layer made of a perforated thermoplastic synthetic resinous film and a lower layer made of thermoplastic synthetic fibers having a hydrophilic property higher than that of the upper layer. These upper and lower layers are intermittently heat sealed together except at a central zone of the napkin by thermally debossing the upper and lower layers so that the central zone may be thicker and softer than the remaining zone.

7 Claims, 4 Drawing Sheets

SANITARY NAPKIN

This application is a continuation of application Ser. No. 08/546,256 filed Oct. 20, 1995, now abandoned.

BACKGROUND OF THE INVENTION

The present invention relates to a sanitary napkin and, more particularly, to a sanitary napkin or a menstruation pad for absorbing menstrual discharge.

A known0 sanitary napkin of a so-called convex type has a central zone that is significantly thicker than a remaining zone. For example, Japanese Utility Model Laid-Open Application No. Sho58-13227 discloses a napkin of a convex type formed by placing upon an upper surface of a lower absorbent layer an upper absorbent layer which is narrower but thicker than the lower absorbent layer.

However, the conventional napkin as mentioned above is disadvantageous in that the convex zone destined to contact a wearer's private parts, particularly the labium, causes a noticeable feeling of incompatibility and, in practical use, is difficult to maintain in close contact with the labium, since the convex zone has substantially the same rigidity as that of the remaining zone. In consequence, convexity of the central zone is often meaningless and causes leakage of menstrual discharge.

SUMMARY OF THE INVENTION

It is a principal object of the invention to provide a convex zone which is softer than the remaining zone.

The object set forth above is achieved, according to the invention, by a sanitary napkin generally comprising a liquid-permeable top-layer, a liquid-impermeable back-layer, and a liquid-absorbent core disposed between these two layers.

The top-layer comprises an upper layer made of a thermoplastic synthetic resinous material and a lower layer of thermoplastic synthetic fibers which are hydrophilic than the upper layer. The upper and lower layers are intermittently heat-sealed together except at a central zone of the napkin by thermally embossing the upper and lower layers. The central zone is thicker and softer than the remaining zone.

With the sanitary napkin of the invention, the central zone (preferably a convex zone) of the top-layer can be maintained in soft but close contact with the labium to effectively prevent menstrual discharge through a gap which would otherwise be formed between the absorbent surface and the wearer's skin.

DETAILED DESCRIPTION OF THE EMBODIMENT

Figure 1:
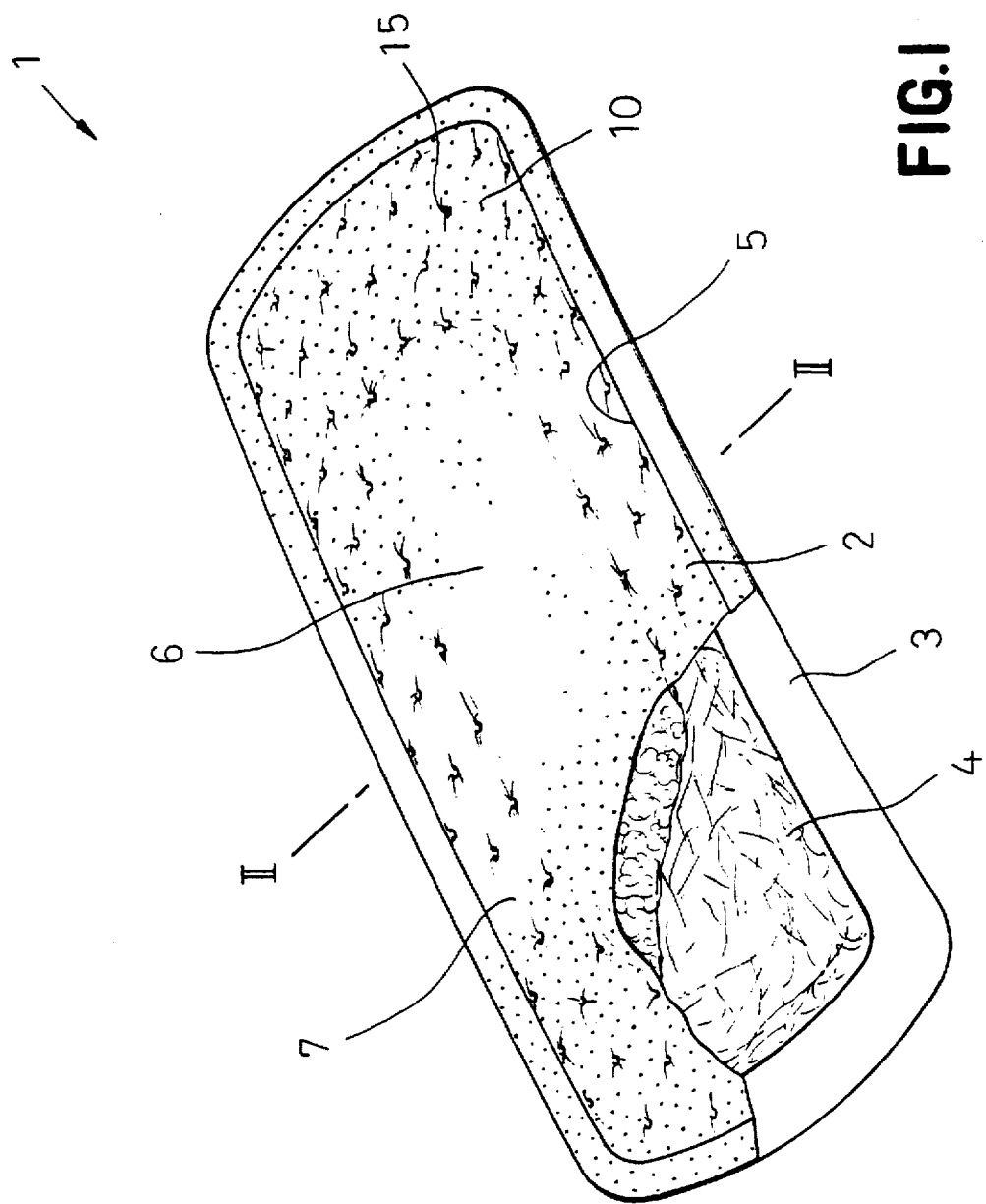
FIG. 1 is a perspective view of a sanitary napkin of the invention as partially broken away.
Figure 2:
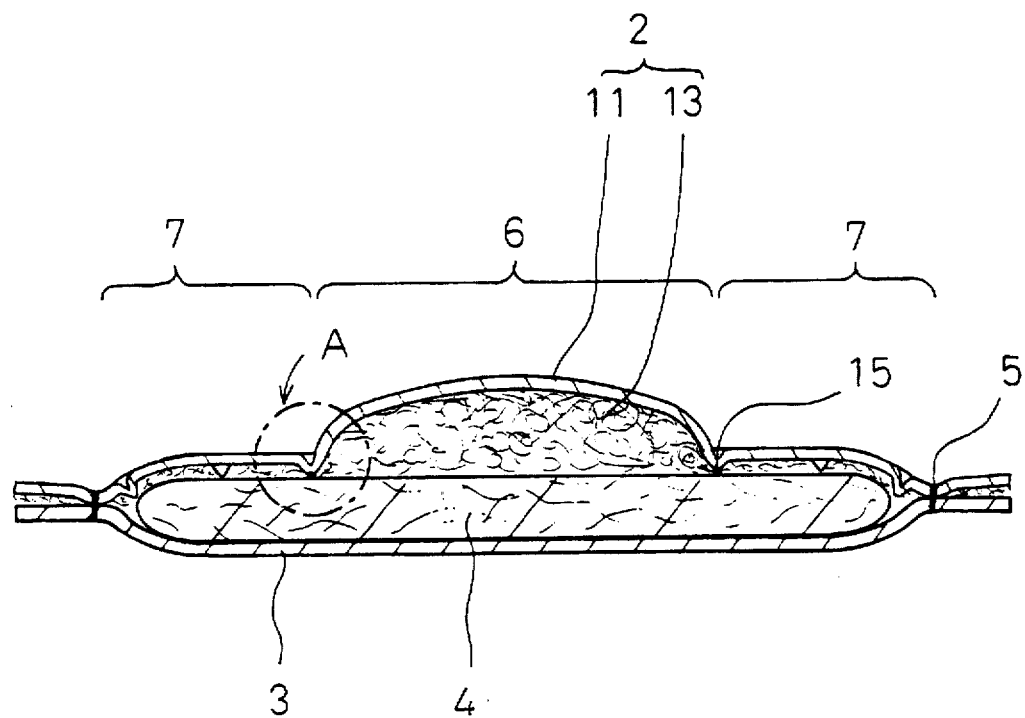
FIG. 2 is a section view taken along a line II—II in FIG. 1.

Referring to FIGS. 1 and 2, a napkin 1 comprises a liquid-permeable top-layer 2, a liquid-impermeable back-layer 3 and a liquid-absorbent core 4 disposed between these two layers 2, 3. Portions of the top- and back-layers 2, 3 extending outward beyond a peripheral edge of the core 4 are bonded together along a seal line 5.

The top-layer 2 is protuberant at a longitudinally as well as transversely extending central zone 6 relative to a zone surrounding this central zone, i.e., the remaining zone 7. The back-layer 3 is made of a thermoplastic synthetic resin film and core 4 comprises a molded fluff pulp having a uniform thickness. The napkin 1 assembled from these components presents an appearance of so-called convex napkin.

Figure 3:
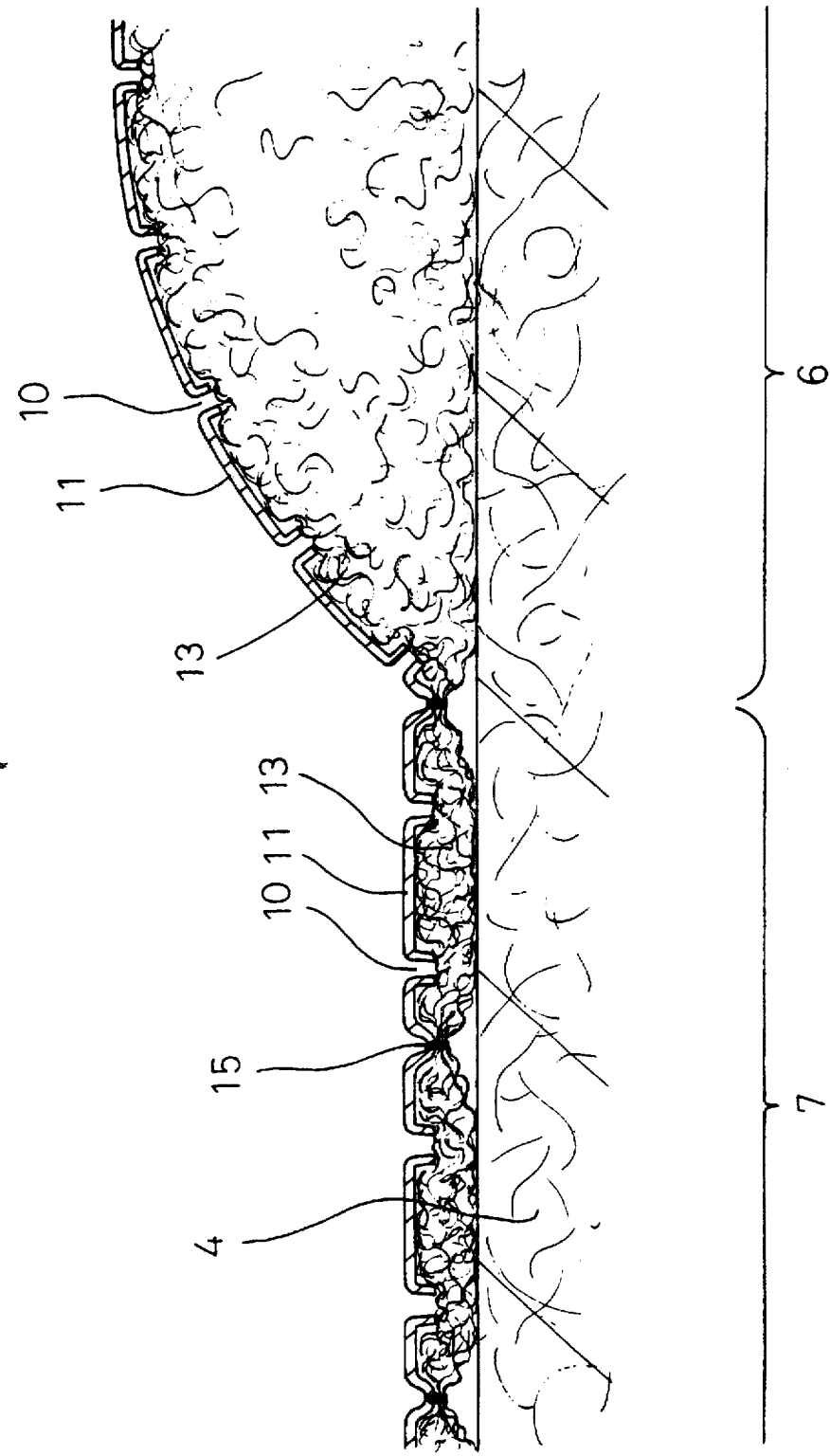
FIG. 3 is a fragmentary sectional view depicting, in an enlarged scale, a top-layer.

Referring to FIG. 3, the top-layer 2 actually comprises an upper layer 11 made of a thermoplastic synthetic resin film formed with fine liquid-permeable perforations 10 and a lower layer 13 made of thermoplastic synthetic fibers. The lower layer 13 may be made of a nonwoven fabric. These upper and lower layers are bonded together at intermittent heat-sealing spots 15 formed by thermal embossing of the surrounding zone 7. The lower layer 13 is in a compressed state within the surrounding zone 7 but softer over the central zone 6 (not subjected to thermal embossing) than the surrounding zone 7. The lower layer 13 has previously been treated to have a hydrophilic property higher than that of the upper layer 11 but lower than that of the core 4. A napkin 1 formed with a top-layer 2 allows the convex central zone 6 to come in close contact with the labium (inclusive of pudendal cleavage) of the wearer's privates so that undesirable leakage of menstrual discharge can be reliably prevented and a quantity of menstrual blood discharged onto the central zone 6 can permeate the top-layer 2 at the central zone 6 into the core 4 underlying the central zone 6.

Figure 4:
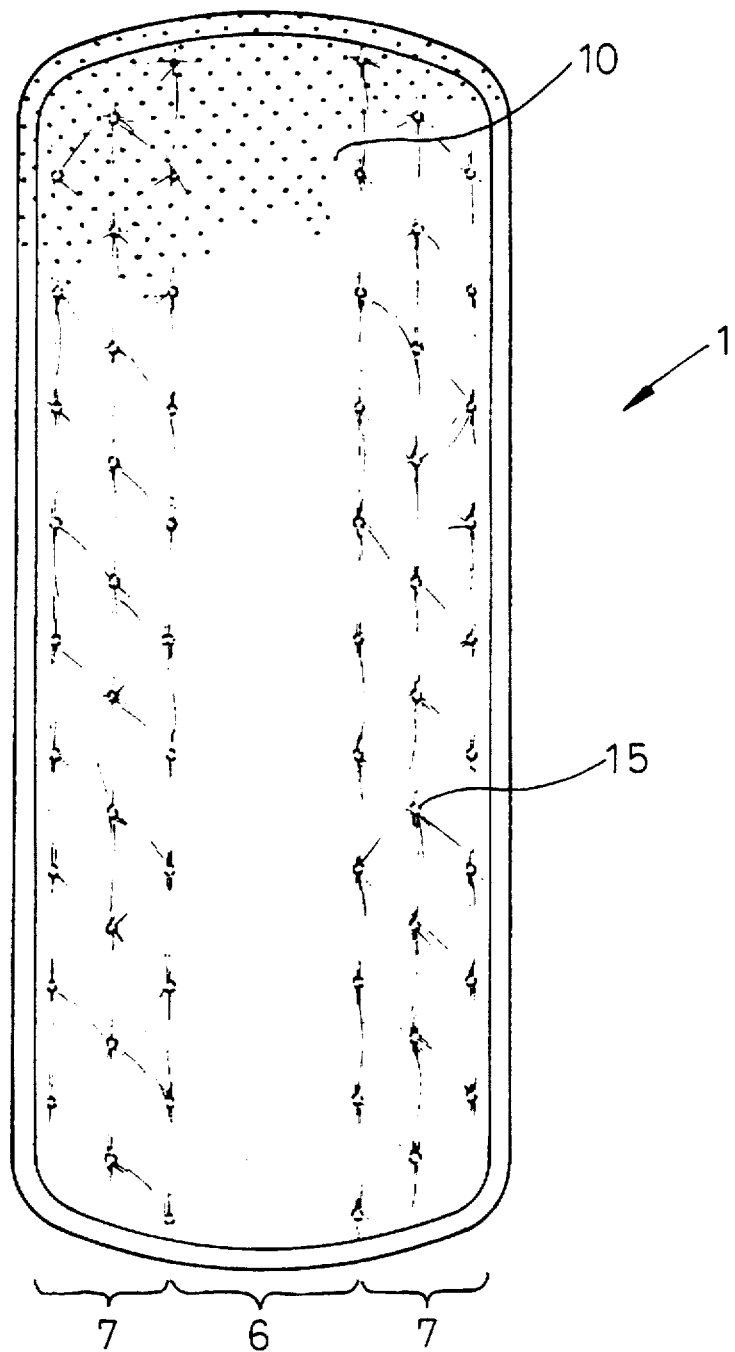
FIG. 4 is a plan view showing a variant of the sanitary napkin of FIG. 1.

Referring to FIG. 4, the napkin 1 has only its transversely opposite sides thermally embossed so that the convex central zone 6 extends fully between longitudinally opposite ends of the napkin 1.

For the invention, the perforated film forming the upper layer 11 may be such film disclosed in Japanese Patent Laid-Open Application No. Hei4-89054. It is also possible to replace the film by a nonwoven fabric of thermoplastic synthetic fibers. In this case, the upper layer 11 of nonwoven fabric is preferably treated to have a hydrophilic property lower than that of the lower layer 13 used as the lower layer of the top-layer 2 to thereby accelerate transfer of menstrual discharge from the upper layer 11 to the lower layer 13.

In the foregoing nonwoven fabrics, individual fibers may be mechanically intertwined, or intertwined under the effect of heat sealing or under the effect of adhesive e.g., hot melt adhesive. The core 4 may also comprise a mixture of fluff pulp with superabsorbent polymer powders.

The sanitary napkin according to the invention not only gives a wearer's privates no feeling of incompatibility but also comes in close contact with the labium inclusive of the pudendal cleavage to prevent menstrual discharge from leaking, since the top-layer is convex and the convex zone is softer than the remaining zone. Furthermore, the top-layer comprises the integrally heat sealed upper and lower layers and, with the napkin being placed against a wearer's body, these two layers advantageously prevent interlayer separation and/or irregular wrinkles which would otherwise adversely affect possibly absorptive properties.

What is claimed is:

1. A sanitary napkin comprising:

a liquid permeable top layer;

a liquid impermeable back layer;

a liquid absorbent core disposed between said top layer and said back layer;

said top layer having a central zone and side zones at both sides of said central zone, said top layer including an upper layer of a thermoplastic synthetic resinous material and a lower layer of thermoplastic synthetic fibers which is more hydrophilic than said upper layer but less hydrophilic than said core;

said upper and lower layers being intermittently bonded together by thermally embossing said side zones; and said central zone being thicker and softer than said side zones.

2. A sanitary napkin according to claim 1, wherein said lower layer is compressed within said side zones.

3. A sanitary napkin according to claim 1, wherein said lower layer is coextensive with substantially an entire surface of said upper layer.

4. A sanitary napkin according to claim 1, wherein portions of said top layer and said back layer extending outward beyond a peripheral edge of said core are bonded to together by a seal line.

5. A sanitary napkin according to claim 1, wherein said core comprises a molded fluff pulp having a uniform thickness.

6. A sanitary napkin according to claim 1, wherein said thermoplastic synthetic resinous material is a fibrous nonwoven fabric.

7. A sanitary napkin according to claim 1, wherein said thermoplastic synthetic resinous material is a perforated film.

* * * * *